United States Patent [19]
Berger

[11] Patent Number: 5,735,692
[45] Date of Patent: Apr. 7, 1998

[54] LASER WELDED INVESTMENT CAST DENTAL RESTORATION, METHOD OF MAKING SAME AND WAX PATTERN MAKING METHOD THEREFOR

[75] Inventor: Robert P. Berger, Encino, Calif.

[73] Assignee: belle de st. clair, inc., Chatsworth, Calif.

[21] Appl. No.: 619,016

[22] Filed: Mar. 20, 1996

[51] Int. Cl.$^6$ .................................................. A61C 11/00
[52] U.S. Cl. ........................................ 433/213; 433/223
[58] Field of Search ............................ 433/34, 202.1, 433/206, 213, 219, 223, 183; 164/69.1, DIG. 4; 264/16, 19

[56] References Cited

U.S. PATENT DOCUMENTS

| | | | |
|---|---|---|---|
| 3,808,687 | 5/1974 | Millet | 433/213 |
| 4,740,160 | 4/1988 | Hruska | 433/206 |

OTHER PUBLICATIONS

Dental Laboratory Technology, Fixed Restorative Techniques, Operative Crown and Bridge, by Henry V. Murray, B.S., D.D.S. and Troy B. Sluder, D.D.S., M.S., 1972 University of North Carolina; "I ntroduction to Fixed Restorative Techniques", pp. 1–7; Types of Fixed Restorations, pp. 15–16; Impressions, Casts and Dies, pp. 29–30; Wax Patterns, pp. 123–124; Spruing and Investing, pp. 149,154–157; Wax Elimination and Casting, pp. 167, 171–172; Soldering, pp. 197–212; All-Metal Bridges, pp. 243–252.

American Recovery, Excel Laser Welder Dental Laboratory Technique Manual.

*Primary Examiner*—Cary E. O'Connor
*Attorney, Agent, or Firm*—Wood, Herron & Evans, L.L.P.

[57] ABSTRACT

A method of investment casting a dental restoration and a dental restoration made, thereby and a pattern therefor, include, in the preferred embodiment thereof, the forming of a wax pattern that includes at least two wax retainers interconnected by a wax link that includes a separable link made of a preformed wax pair of blades with confronting parallel identically shaped surfaces in prepositioned intimate contact. The link is preferably set into a slot of the same thickness as the link cut into the connector of the pattern as the retainers are mounted on precisely positioned models of tooth abutments, and waxed to the connector faces exposed by the cut. The link is then separated to divide the pattern into two components from which corresponding sections of the restoration are cast by the lost wax investment casting method. The cast sections so formed have weldable faces thereon corresponding to the interface surfaces of the link blade of the pattern components. The faces are laser welded together, being dimensioned to a width that is between one and two times the effective welding depth of the focused laser beam so that the faces can be welded together across their entire areas from two opposite edges of the faces.

24 Claims, 3 Drawing Sheets

LASER WELDED INVESTMENT CAST DENTAL RESTORATION, METHOD OF MAKING SAME AND WAX PATTERN MAKING METHOD THEREFOR

The present invention relates to dental restorations, and particularly to the manufacture of bridges and other restorations that anchor to more than one tooth of a patient.

BACKGROUND OF THE INVENTION

The use of a dental restoration such as a dental bridge is typical in a situation where there are two teeth in reasonably good condition between which there is a vacant location from which a tooth is missing. A restorative solution in such a situation involves the creation of a dental prosthesis such as a bridge that consists of a crown for each of the two good teeth with a false tooth located between the two crowns to substitute for the missing tooth. The false tooth, which is called the pontic, and the two crowns, which are called retainers, are typically formed as an integral one-piece unit. The two good teeth are ground to form posts, called abutments. The bridge is installed with each of the retainers fitted on a respective one of the abutments supporting the intervening pontic therebetween to occupy the position of the missing tooth. Dental splints are formed in a similar way, without the intermediate pontic.

In a common situation where a crown or retainer is to be secured to a structurally sound tooth, the first step is to grind the tooth to a generally thimble shape to form the abutment. The crown, which is fitted over the abutment, becomes a retainer to anchor the restoration. In the situation of where a bridge is built so to support a false tooth or pontic, two retainers are anchored on either side of the position of the missing tooth, with the pontic rigidly linked to the two retainers by way of two connectors. One of the connectors rigidly interconnects the pontic to one retainer on one side of the pontic while the other connector rigidly interconnects the pontic to the retainer on the other side of the pontic. Such a bridge, or at least the structural framework thereof, is typically cast out of a single material, such as gold.

The casting of a dental restoration such as a gold bridge is conventionally accomplished by a process known as the lost wax investment casting method, which has long been used in the jewelry making art. In the investment casting method, a pattern of the two retainers and the pontic is first carved or otherwise built up out one or more specially developed types of wax. The pattern formation often is started by a dentist making an impression of the abutments and space formerly occupied by the missing tooth, as well as an impression of the occluding teeth. With the impression used as a mold, a gypsum casting is then made of the section of the patient's mouth in which the bridge must fit. From the gypsum casting, the individual teeth are then segmented, and the segmented teeth are reassembled on dowel pins into a model of the patient's jaw or jaws. Using the model, the pattern of the restoration is then carved in wax so as to restore the model to the final condition being sought by the dentist.

In the conventional formation of a metal bridge, the wax bridge is replicated in metal using the lost wax investment casting process. This process continues with the mounting of the wax pattern on a meltable stand that includes wax supports that are to form the sprue holes of a mold. The wax pattern and stand are then placed in a cylinder or flask. An investment material in the form of a powder and water mixture is placed in the flask to completely fill the space around the stand and pattern. When the investment material has hardened, the hardened investment material and the stand and pattern contained therein are placed in an oven where the assembly is heated to the point where the material forming the pattern and stand not only melts and drains from the downwardly facing hole, which was occupied by the support for the pattern on the base of the stand, but completely evaporates so that the wax and the material forming the pattern and stand are totally removed from the investment material. This leaves a mold formed of the investment material, with the space formerly occupied by the wax forming a mold cavity in the shape of the pattern, complete with one or more sprues.

To form the restoration out of gold, the investment material is invested so the hole faces up and molten gold is then poured or injected into the mold through at least one of the sprue holes. The filling of the cavity can be facilitated by using techniques, such as centrifugal casting, well known in the art. When the gold has cooled and hardened, it tends to contract somewhat. The amount of this contraction is predictable, and the water to powder ratio of the investment material can be controlled so that its expansion and contraction properties in its hardening process and upon heating and cooling, compensate for the dimensional changes of the gold. When the gold has hardened, the investment material is then broken away, leaving an integrally formed cast gold restoration or restoration framework that is in the former shape of the wax pattern, with a gold replica of the gold sprues and stand also integrally attached. The gold restoration is then cut from the gold sprues.

In the case of a dental restoration that must be fit onto more than one abutment formed on plural teeth or other fixed points in the mouth of the patient, several factors affecting the lost wax investment casting process have resulted in the introduction of dimensional errors that prevent the rigid, integrally formed, cast gold retainers from properly fitting on their respective abutments. For a proper fit for a bridge, for example, the distance between retainers should be within 100µ or less of the actual distance between the abutments in the patient's mouth, depending on the application. Where structure such as dental restorative implants are used, for example, which are directly secured into the bones of a patient's jaw, even 100µ of error is too large, with tolerances on the order of 10µ to 25µ being required. The production of excessive tolerances in the traditional lost wax investment casting process is due to many causes, including deformations of the wax pattern in its handling and in its production. Where, for example, abutments are somewhat non-parallel, the placement on and removal from a cast or model thereof can result in deformation of the pattern. Where the restoration is of substantial length or covers a large number of teeth, the wax pattern is subjected to many small stresses in handling, which can bend such a pattern to the point that the resulting gold casting is out of tolerance at some of its points of rigid connection to the dental anatomy of the patient.

Prior attempts to solve the excessive tolerance problem have been complicated and time consuming, and most often have involved the cutting of one of the connectors between pairs of retainers and then resoldering the cut connector by an investment soldering process. This cutting and soldering process removes a thin section of the gold material and shortens the dimension of the restoration between the retainers. To this, cut material can be further removed or added until the inter-retainer distance is hopefully equal to that between the two abutments to which the retainers must connect. This process and the other processes of the prior art discussed herein are described in a publication Henry V.

Murray and Troy B. Sluder published in 1972 by the University of North Carolina and entitled *Dental Laboratory Technology, Fixed Restorative Techniques,* which is hereby expressly incorporated herein by reference.

When the connector of the cast rigid structure of a restoration is cut, the investment soldering process that is used includes steps intended to take into account the thermal expansion of the materials, including the gold, the solder and the investment material on which the two parts to be soldered are supported, as well as the shrinkage of the soldered assembly as the solder solidifies and cools. The investment material is selected and configured so that the gap to be soldered remains relatively constant in the heating and cooling process at about 0.005 to 0.01 inches, for example, at about 0.003 inches. When the pieces to be joined are accurately related, either on a working cast or in the patient's mouth, the relationship must be accurately transferred, which is accomplished by using a plastering index or a fast setting resin. Then, a soldering investment is prepared in a multiple step process that includes a preparation of the investment assembly, trimming of the investment block, boiling out of any waxes that have been used in the investment forming process and fluxing of the work. Then solder is selected, the parts are preheated and contaminants are burned out in a process that requires considerable skill to avoid damage to the parts and the assembly. Solder must be applied with special care taken to avoid oxidation or other contamination of the material. The completed solder joint is then trimmed and polished. Notwithstanding this laborious process, the resulting solder joint is weaker than was the original cast metal connector, and thus results in a structurally weak point in the restoration that is prone to failure.

It has been proposed, but never successfully achieved, to eliminate the investment soldering process and to replace that process with a laser welding process. In a laser welding process, it is essential that the two parts of the metal restoration that are to be welded together present smooth flat surfaces or faces that are in contact with each other, without any gap between them that typically exists in soldering and other joining methods. Unfortunately, cutting of the cast metal restoration into two pieces leaves a gap across which the faces cannot be rejoined by laser welding. Further, the need to readjust the dimension or angle between the two parts, which is the reason that the restoration would have been cut in the first place, will either produce a gap bounded by sides that may or may not be parallel, or will require that the facing surfaces of the cut be machined so that the parts can be moved more closely together, which introduces dimensional errors that inhibit correct fit.

An alternative to cutting the casting would be to perform the cut on the wax pattern, to re-form the cut surfaces of the pattern, and then to cast the restoration in more than one part, with the goal of laser welding the parts of the metal casting together to form the restoration. However, no way to successfully carry out such an approach has been provided in the prior art. The forming of a two part pattern from which can be produced a casting with laser weldable faces has not been accomplished. The cutting of the wax pattern invariably leaves a gap. Rebuilding of the surfaces that are to produce the cast faces that are to be welded together, that is the surfaces of the pattern that are facing the gap, requires the manual addition of wax to build up the surfaces. Each of the surfaces must then be made flat, smooth and parallel so that the corresponding faces of the cast metal parts will be capable of welding together with a laser welder, without the need to remove from the metal faces an undue amount of material by machining or polishing. This problem would exist for fusing techniques other than laser welding, where the material at the faces is to be made flowable by focused or otherwise localized energy and fused together. This manual process of so flattening and smoothing the pattern surfaces can take up to an average of about fifteen minutes per cut. With a restoration that will, in its completed integral form, mount, for example, to six or eight abutments, an additional two hours of technician's time could be required. Such an expenditure of time is not acceptable cost in a laser welding process.

The process of the prior art that includes the cutting and resoldering of an integrally cast dental restoration designed to be supported on more than one abutment in the patient's mouth has been slow, expensive and prone to error and inaccuracy, and has resulted in a restoration that is structurally inferior to the integrally formed restoration. Mere replacement of the cutting and investment soldering of the metal casting by laser welding separately cast restoration parts requires precision in wax pattern making that is beyond that produced by the standard wax forming techniques, and requires additional wax pattern making steps that add to the time and cost of the laser welding process. Accordingly, there is a need for an improved process that is more accurate, easier to perform and less expensive, and results in an improved dental restoration.

SUMMARY OF THE INVENTION

It is an objective of the present invention to provide a method of precisely achieving a desired distance between two points on a dental restoration at which the restoration connects to the patient's dental anatomy. It is a particular objective of the present invention to provide a method by which such precise spacing can be achieved in the manufacture of a dental restoration where the restoration is to include a one piece rigid structure, such as a metal framework, formed by the lost wax investment casting method.

- It is a further objective of the present invention to facilitate the use of more efficient and effective methods of joining separate or separated sections of the metal framework or other rigid structure of a dental restoration, and particularly to eliminate the investment soldering process and to provide for the use of fusing techniques, such as laser welding or some other localized energy directing technique, for joining the sections of the restoration. It is a particular objective of the present invention to provide a method of casting a metal portion of a restoration in separate sections, especially with precisely located and shaped interface surfaces or faces by which the sections can be precisely laser welded together, and more particularly, to provide for the formation of precision wax patterns from which the separate metal sections can be precisely cast.

Based on the principles of the present invention, there is provided a method by which separate wax pattern components are formed for each of the corresponding sections of a restoration, preferably of the framework thereof. The separate pattern components are formed so that the separate sections of the restoration can be cast to provide connection of each section to preferably only one point on an abutment or other anchoring structure that is fixed relative to the dental anatomy of the patient. Such anchoring structure might include an abutment formed of a tooth, an implant fixed to a jaw bone, or on some other such structure. The method particularly provides for the formation of a pattern from which can be cast the framework or other rigid structural sections of a restoration with each section having one or more fusible faces thereon, such as surfaces that can be laser welded to a mating face on an adjacent section.

According to the preferred embodiment of the present invention, a method is provided for forming a one piece dental restoration that is of a prescribed configuration for connection to the dental anatomy of the patient, or to anchoring structure fixed relative thereto, at least two fixed points. The method includes the formation of a wax pattern, such as a pattern suitable for use in a lost wax investment casting process. The pattern is formed by shaping the wax pattern in at least two parts or components, with each component including a wax retainer for connection to an abutment or other structure at a point on or otherwise fixed to the patient's dental anatomy. The pattern includes a wax link formed in two pieces or elements, with each element being integrally waxed to one of the pattern components. The cooperating or mating link elements on the respective pattern components each have confronting interface surfaces thereon that are in intimate face-to-face contact with each other when the pattern components are arranged in the prescribed configuration of the dental restoration. The interface surfaces of the cooperating link elements have predetermined dimensions, preferably including a constant width or transverse extent or dimension that is measured in a direction parallel to the interface surfaces that allows the use of a laser welder or other fusing technique, particularly a technique having a fixed welding depth to fuse the link across the entire width of the faces of the casting that correspond to the interface surfaces of the pattern. Such a depth is generally a function of the parameters or properties of the laser or other localized energy, depending on properties such as the wavelength or focusing optics of the laser, or on the properties of the material to be fused, such as its transparency or absorbency to the energy used. By correlating the dimensions of the interface surface to the properties of the localized energy used to weld or otherwise fuse the mating faces of the adjacent cast sections, the entire extent of the interface surfaces, when replicated in the casting made from the pattern, can be effectively fused together from the opposite sides or edges of faces on the castings of the dimensions of the interface surfaces, thereby forming a strong connection. Preferably the wax link that forms the interface surfaces in the wax pattern is made by waxing a preassembled two piece split blank, of the predetermined dimensions, into a gap or slot formed between two adjacent components of the pattern that are prearranged on a working model of the patient's mouth.

In accordance with the preferred embodiment of the present invention, a metal framework or other rigid structure of the restoration is formed by the lost wax investment casting process, wherein separate mold cavities are formed from each of the pattern parts, and separate sections of the rigid structure are cast in each of the cavities from a metal or other fusible material, preferably of gold, with each of the sections corresponding in shape to one of the components of the pattern. As a result, the separate cast sections each have a weldable or other fusible face thereon of the same predetermined extent or dimensions as of the interface surfaces of the pattern components that formed the cavities in which the sections were cast. These sections are then arranged in the prescribed configuration that they will take in the finished one piece structure, with the fusible faces of the adjacent sections in intimate contact with each other. When the fusible faces of the sections are made of gold or other such metal or weldable material, they can then be welded together by directing the focal point of a laser beam from a laser welder at the edge of the confronting faces of the two sections that are in intimate contact with each other, with the beam parallel to the faces. The laser beam is moved along the edges at the opposite transverse sides of the faces. Similar fusing of the faces can be carried out where the faces are formed on other materials, such as a vitreous ceramic or high density fusible polymer material. Fusing can be carried out with other than focused laser beams, such as by using other types of focused or otherwise localized radiant or wave energy or the like.

In the most preferred embodiment, for laser welding of metals such as gold, the predetermined width of the fusible faces is preferably slightly more than the maximum effective depth of the laser welding beam, but less than twice the effective welding depth, or approximately 3 millimeters for a commercially available neodymium YAG lasers, which are preferred, which has a welding depth of slightly more than 1.5 mm. The welding results in the formation of a one-piece metal restoration framework or other rigid restoration structure of the prescribed configuration, in which the distance between adjacent cast retainers of the finished restoration are equal to the distance between two abutments formed of the patient's teeth, or of implants made into abutments fixed to the patient's jaw bone, or of other structures fixed relative to the dental anatomy of the patient, to which the retainers are to mount. The metal framework is machined, polished, laminated with ceramic or otherwise finished to form the completed dental restoration, which can then be installed in the patient's mouth.

Further in accordance with preferred embodiments of the invention, a method is provided wherein the wax pattern is first formed as an integral form that includes at least two retainers, each of which is configured for rigid attachment to the dental anatomy of the patient. The retainers of the pattern are interconnected by an intermediate wax connector. In lieu of casting the full pattern as a single piece or waxing separable links into the pattern in the first instance, the pattern is separated into the components by removing a transverse segment of the wax connector of a fixed thickness, measured along a line interconnecting the retainers and perpendicular to the plane of the cut, to form a fixed thickness slot entirely through the wax connector. Preferably, the connector segment is removed with a chisel or other wax cutting tool to produce precisely spaced parallel sides that are spaced apart to define the connector slot having a thickness of approximately the same thickness as the combined thickness of the blades of the two piece, split blank of which the wax link is formed. Such a split blank is preferably formed by detachably joining preformed blank halves that collectively have a thickness approximately equal to the fixed thickness of the connector slot. Such a split blank is made part of the pattern by waxing each blade to a respective one of the pattern components that are adjacent the slot, so that each of the blades forms one of the wax link elements. The detachable connections that hold the blades temporarily together are preferably made of wax and can be removed with a chisel or other tool when the link has been waxed into the pattern.

In accordance with a preferred application of the present invention, the restoration is a dental bridge or splint with each of the retainers thereof being configured to be rigidly mounted to a fixed abutment formed on a respective one of the patients teeth. With a splint, the abutments are formed on two teeth that are usually adjacent, with the retainers joined by a single connector. In the shaping step, one of the two components of the pattern is formed to include one of the elements of the wax link and one of the wax retainers, while another of the components of the pattern includes the other wax retainer and the other element of the wax link. With a bridge, the abutments are formed on teeth that are adjacent one or more locations of missing teeth to be restored by the bridge. Such a bridge has a bridging portion that includes at least one pontic that is joined by two connectors, each fixed between a respective one of the retainers and the pontic. In the shaping step for the bridge, one of the two components of the pattern is formed to include one of the elements of the wax link, at least one wax pontic and one of the wax retainers, while the other component includes at least the other wax retainer and the other element of the wax link. With a bridge, the wax link may lie between two wax pontics, one on each of the components of the pattern.

These and other objectives of the present invention can be appreciated from the following detained description of the drawings in which:

DETAILED DESCRIPTION OF THE PREFERRED EMBODIMENT

The preferred embodiment of the invention is described for a case in which the entire upper dental arch of a patient is to be fitted with a solid one piece restoration. The illustrated and described example represents the creation of a solid one piece metal framework for a full arch restoration for a patient who is missing the upper right first bicuspid and the upper left first and second bicuspids and whose remaining upper teeth require crowns. For such a patient, the restoration includes a upper single pontic bridge supported on adjacent abutments on the upper right cuspid and second bicuspid and a two pontic bridge supported at least on the upper left cuspid and first molar. In lieu of one or more of the abutments being formed of the patient's teeth, an abutment may be formed of a dental implant or other structure that is fixed relative to the jaw bone or other dental anatomy of the patient.

Figure 1:
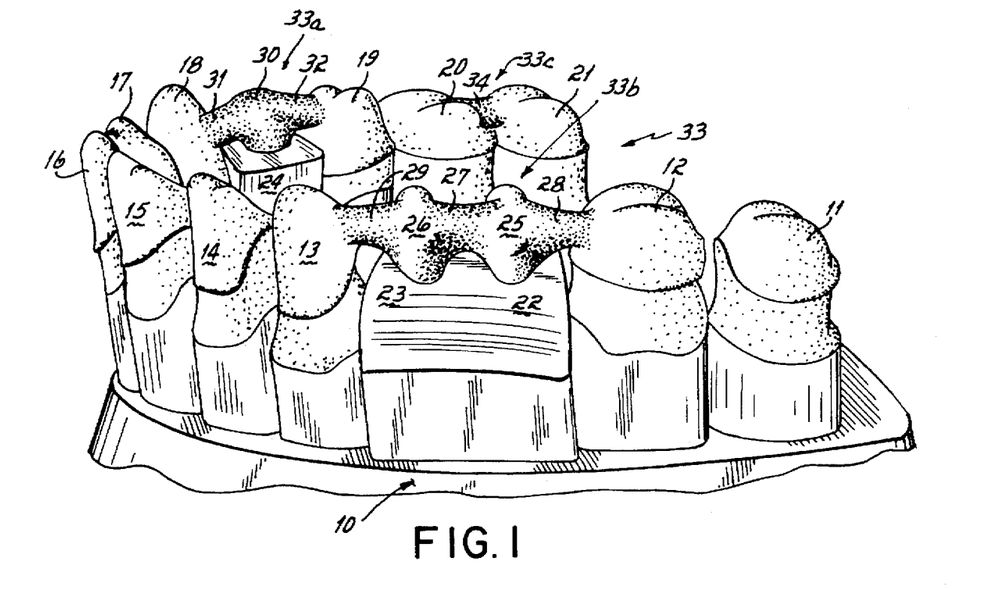
FIG. 1 is a perspective view of a working dental model having a wax pattern thereon in accordance with certain steps of one embodiment of the method of the present invention.

The construction of such a restoration is begun by using standard impression and wax pattern forming techniques to produce a full maxillary model 10, with wax copings 11–21 representing each of the teeth present on the patient's upper arch, as illustrated in FIG. 1. Three empty spaces 22–24 represent the positions of the missing upper left second, left first and right first bicuspids, respectively. Continuing with the use of conventional wax pattern forming techniques, a pair of wax pontics 25 and 26 is formed to occupy the spaces 22 and 23, respectively, with pontics 25 and 26 interconnected by a wax connector 27 and each respectively connected to adjacent wax abutment copings 12 and 13, respectively, by connectors 28 and 29. Similarly, a single pontic 30 is formed to occupy the space 24 and is connected to the adjacent wax abutment copings 18 and 19 by connectors 31 and 32, respectively. Where the restoration is to be a full arch restoration, all of the remainder of the copings are joined to adjacent copings by splint connections to form a complete single piece wax pattern 33. One such splint connection is shown in FIG. 1 as connector 34 between copings 20 and 21. Not all of such connectors 34 are shown in FIG. 1 for interconnecting all of the copings of a full arch pattern 33, but rather connectors 27–29, 31–32 and 34 are illustrated, which are those connectors required for formation of a less than full arch patterns, such as single pontic bridge pattern 33a, two pontic bridge pattern 33b and a two coping splint 33c.

The present invention facilitates the formation of one piece restorations by casting their frameworks or other rigid structures in a plurality of separate sections, with each containing preferably only one retainer. This involves the formation of separate wax pattern components, one for each of several separate sections of a multiple section restoration. In the preferred embodiment of the invention, this is achieved by forming the wax pattern, for example, the pattern 33, to have at least one wax connector between each of the wax abutment copings for which a retainer is to be formed. This connector is made to have a separable or detachable wax interface. Such a separable wax connector is formed of a split connector blank 35, as illustrated in FIG. 2.

Figure 2:
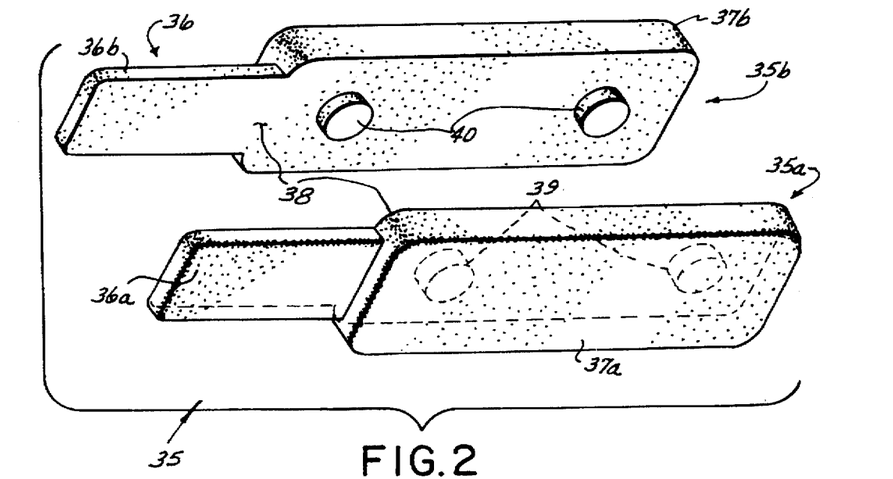
FIG. 2 is an exploded perspective view of a wax connector blank for use in one embodiment of the method of the present invention.

Referring to FIG. 2, the connector blank 35 is formed of two halves or sides including an A-side 35a and a B-side 35b. Each of the sides 35a,35b includes a respective blade 36a,36b of a connector link or link blank 36, each blade being preferably approximately 3 mm wide, 7 mm long and 0.75 mm thick, and a handle 37a,37b, respectively, that is preferably about 15 mm long, 4 or 5 mm wide and 1.5 mm thick. The 3 mm width of the blades 36a, 36b is at least equal to, but not more than twice, the depth attainable by the laser welder that is intended to be used to join the cast sections, as is explained more fully below. The handles 37a,37b are each connected at one of the longitudinal ends thereof to a longitudinal end of the respective connector blade 36a,36b of the link blank 36.

The blades 36a, 36b and handles 37a,37b of each of the sides 35a,35b of the blank 35 are arranged so that an interface surface 38 of each lies in a common plane. Each of the sides 35a,35b of the blank 35 is integrally formed of a high melting point wax, such as that referred to as injection wax of a type, for example, as manufactured and marketed by Belle de St. Claire of Chatsworth, Calif. under its trademark Electra Wax™. A pair of holes 39 is provided in the planar surface 38 of the handle 37a of the A-side 35a of the blank 35, while a pair of fastening posts 40 is provided in the planar side 38 of the handle 37b of the B-side 35b of the blank 35. The posts 40 are configured to snap fit into the holes 39 to fasten the two sides 35a,35b together with the planar surfaces 38 thereof in intimate contact. This forms connector blank 35, having a handle that is 3 mm thick, 15 mm long and 4 to 5 mm wide with a two-layer blade 36 extending from a longitudinal end of the handle. The two-layered blade 36 is 7 mm long, 3 mm wide and 1.5 mm thick, which is the combined thickness of the two blades 36a and 36b. When the blank 35 is assembled, planar surfaces 38 of the blades 36a,36b, which are exactly the same size and shape, coincide exactly so that a laser beam from a laser welder, aimed at the coincident edges of the cast section faces that correspond to the surfaces 38 of the link, and parallel thereto, will not impinge upon one of the faces of the cast section before the other. Otherwise, one face and not the other may be melted. Further, because the width of the surface 38 at the blades 36a, 36b is 3 mm, which is designed to produce a weldable face for a laser having a weld depth of at least, but only slightly more than 1.5 mm, the faces corresponding to entire surfaces 38 of the blades 36a,36b will be welded together when the laser beam is moved along the two opposite side edges thereof.

According to principles of the present invention, between each pair of retainers that are to be formed in a single piece restoration for attachment on two tooth abutments, there is at least one separable connector that is formed, in the first instance, in the wax pattern 33. Such a separable wax connector includes a separable wax pattern link, such as link 44, illustrated between the wax copings 19 and 20 in FIG. 3. The wax link 44 is formed of two link halves or elements 44a,44b, having interface surfaces in intimate contact but not bonded to each other, formed of the pair of blades 36a,36b of one of the separable connector blanks 35, from which the handle portion 37 has been removed such as with a chisel or hot spatula. Such a link 44 can be waxed into the connector in the course of the process of forming the pattern 33. Preferably, however, the link 44 is placed in the pattern 33 to replace a solid connector that has been cut from the wax.

Figures 3, 3A, 3B, 3C:
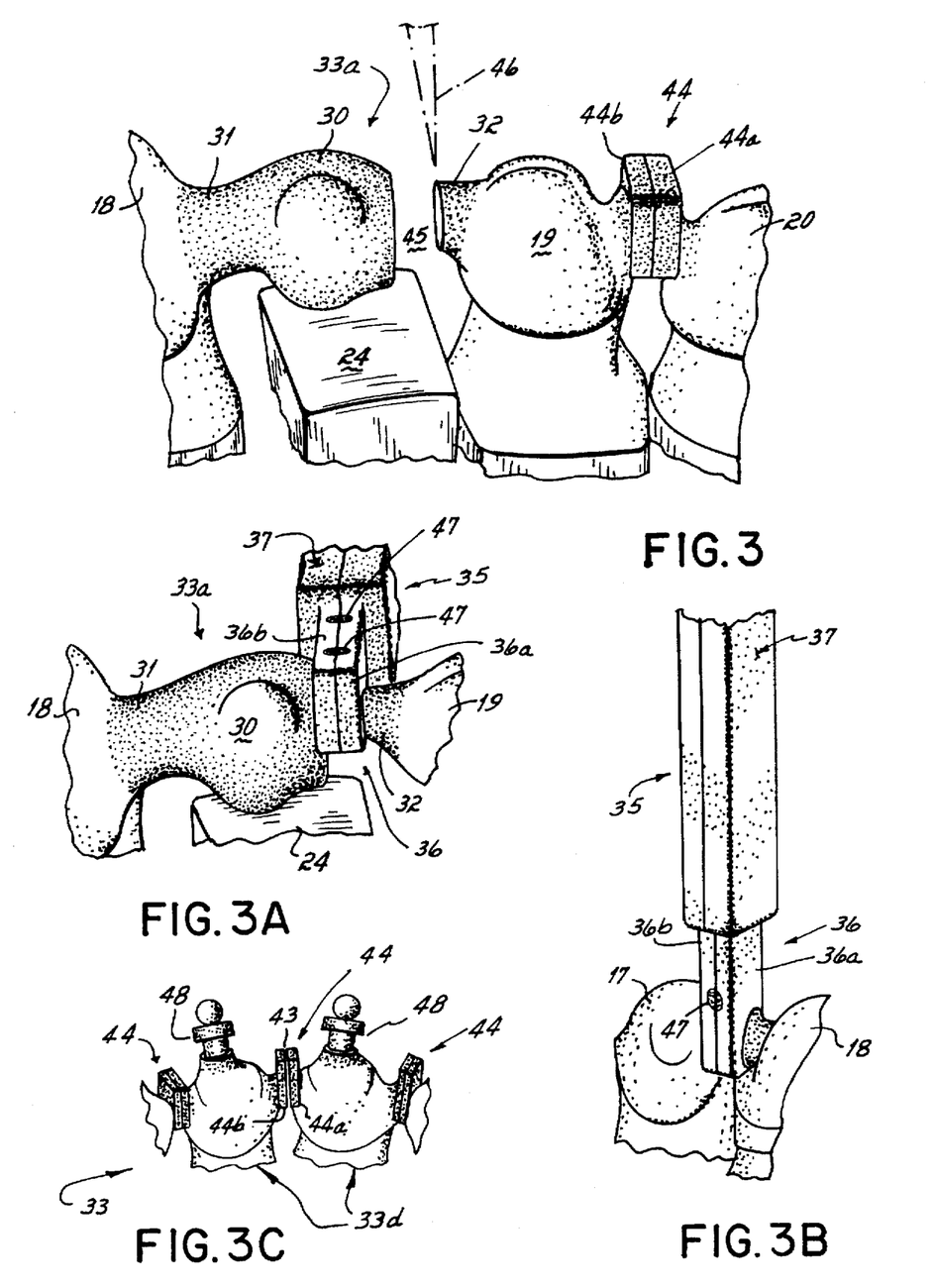
FIG. 3 is a perspective view of a portion of the pattern of FIG. 1 illustrating subsequent steps in preferred embodiment of the method of the invention.
FIG. 3A is a view similar to FIG. 3 illustrating a still further step in the method.
FIG. 3B is a view similar to FIG. 3 illustrating a still further step in the method.
FIG. 3C is a view similar to FIG. 3 illustrating a still further step in the method.

Referring to FIG. 3, a portion of the pattern of FIG. 1 is illustrated, including the copings 18 and 19 and the bridge portion 33a that includes the pontic 30, the connector 31 and the connector 32, which has therein a slot 45 for the insertion of a link 44. The slot 45 is made in the connector 32 and in each connector that is to contain a separable link 44, and has a thickness that is the thickness of the two-layered blade 36 of the blank 35, which is 1.5 mm in the embodiment shown. The slot 45 is cut with cutting tool 46, such as a 1.5 mm chisel carver. While the slot 45 is cut completely through the connector, it is not necessary that the slot 45 be cut to the full thickness of 1.5 mm all the way through the connector, but only as far as the link 44 is to be inserted. The slot 45 should, however, pass entirely through the connector preferably at the center, 0.75 mm from each of the slot sides, so that in the resulting casting, the seam or confronting faces of the casting correspond to the interface surface between the two blades 36a,36b will be accessible to a laser welder from the bottom.

When a slot 45 has been cut, link 44 is formed therein by the insertion of the link blank 36 formed of the blades 36a,36b of one of the blanks 35, as illustrated in FIG. 3A. The blades 36a, 36b are secured to the adjacent parts of the pattern 33 on both sides of the slot 45 by using wax such as Belle de St. Claire Former Wax™ applied with a needle tip, or by using Belle de St. Claire Ultra Wax™ with an Ultra Waxer™ Electronic Spatula. The blades 36a,36b of the link blank 36 of the blank 35 have been tacked together at their edges with small drops 47 of wax to hold the blades 36a,36b in place and prevent wax contraction from pulling the blades 36a,36b apart. The drops 47 as well as the handle 37 of the blank 35 form a detachable connector between the adjacent retainers. The control of heat and the use of low melting point, smooth flowing former wax prevents the contraction of the wax from separating the two blades 36a,36b of the link blank 36. A blank 35 is also illustrated in FIG. 3B waxed into a connector between two anterior tooth copings 17 and 18. The preferred orientation of the blank 35 for the anterior teeth is vertical, as illustrated. When the blades 36a, 36b have been attached to both adjacent parts of the pattern, a hot spatula (not shown) is used to remove the handle portion 37 of the blank 35, leaving the link 44 (FIG. 3C) formed from link blank 36. To finish, the chisel carver 46 is used to remove the droplets of wax 47 that hold the link halves 44a,44b together and to remove the melted surface left when the handle was removed with the spatula. As seen in FIG. 3C, this frees the link along the interface, as shown at 43, between the two parts 44a,44b and disconnects all the adjacent parts of the pattern 33 along their interfaces, leaving the adjacent parts of the pattern in intimate contact, but not joined, resulting in multipart pattern 33d (only a portion of which is shown). When all of the links 44 are inserted in the pattern 33, sprues 48 are attached to each of the separate parts of the multipart pattern 33d. A resulting multipart pattern 33d with all of the parts in place and in mutual contact with the adjacent parts (while not shown) is readily apparent from the foregoing.

Figure 4:
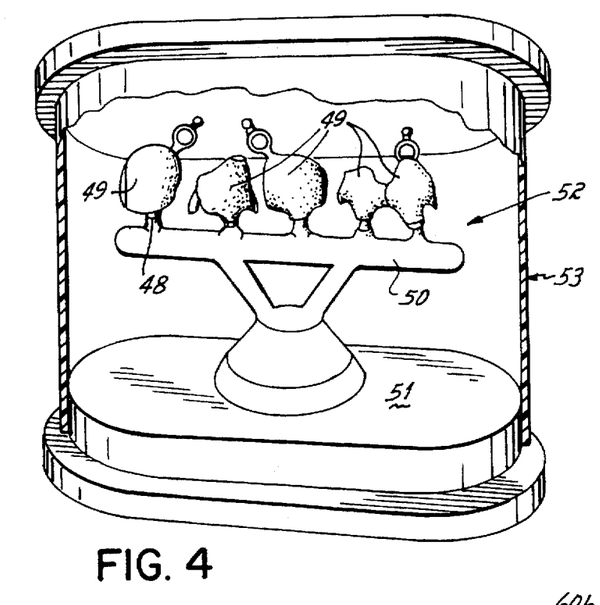
FIG. 4 is a perspective view illustrating components of the pattern of FIGS. 1–3C above prepared for lost wax investment casting.
Figure 4A:
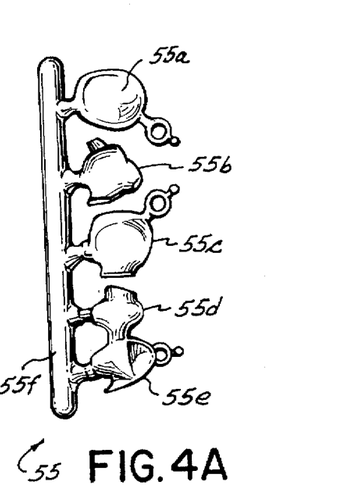
FIG. 4A is a perspective view of a multiple section casting made from the pattern of FIG. 4.

As illustrated in FIG. 4, when the pattern 33 is complete, individual completed wax components or parts 49 of the pattern 33 are separately removed from the model and placed on distribution sprues 50, then mounted to distribution bases 51 to form assemblies representative of a full mold cavity wax pattern 52 for embedding in casting investment. The imbedding is carried out by placing the full cavity pattern 52 in a mold flask or cylinder 53. Then, according to conventional lost wax casting techniques, the flask 53 is filled with investment material, allowed to harden and removed from the flask 53. The hardened investment with the full cavity pattern 52 contained therein is then placed into an oven where the assembly is heated until the wax has melted and drained and evaporated from the investment, forming a hollow mold having a cavity therein of the shape previously possessed by the cavity pattern 52. In this cavity, a metal casting is made by filling the cavity with molten metal, allowing the metal to solidify, breaking away the surrounding investment and removing the casting 55 formed of an integral cast piece of metal that includes the separate cast sections, for example sections 55a–55e attached to a cast replica of the sprue 55f, as illustrated in FIG. 4A. The separate cast sections 55a–55e of the casting 55 are then separated from the cast sprue portion 55f.

In order to provide a way to make corrections where it is found that casting parts, such as a those of a bridge cast in one piece, do not fit, the connector blanks 35 may be cast or otherwise provided in metal to form metal versions thereof. Such metal connector blanks can be used by cutting the bridge into segments which leaves a slot or gap, and using the cast connector blank to fill the gap. The gap will first be ground to leave a space the same dimension as would have been made with the chisel carver when cutting the slot 45 in the wax pattern.

Figure 5:
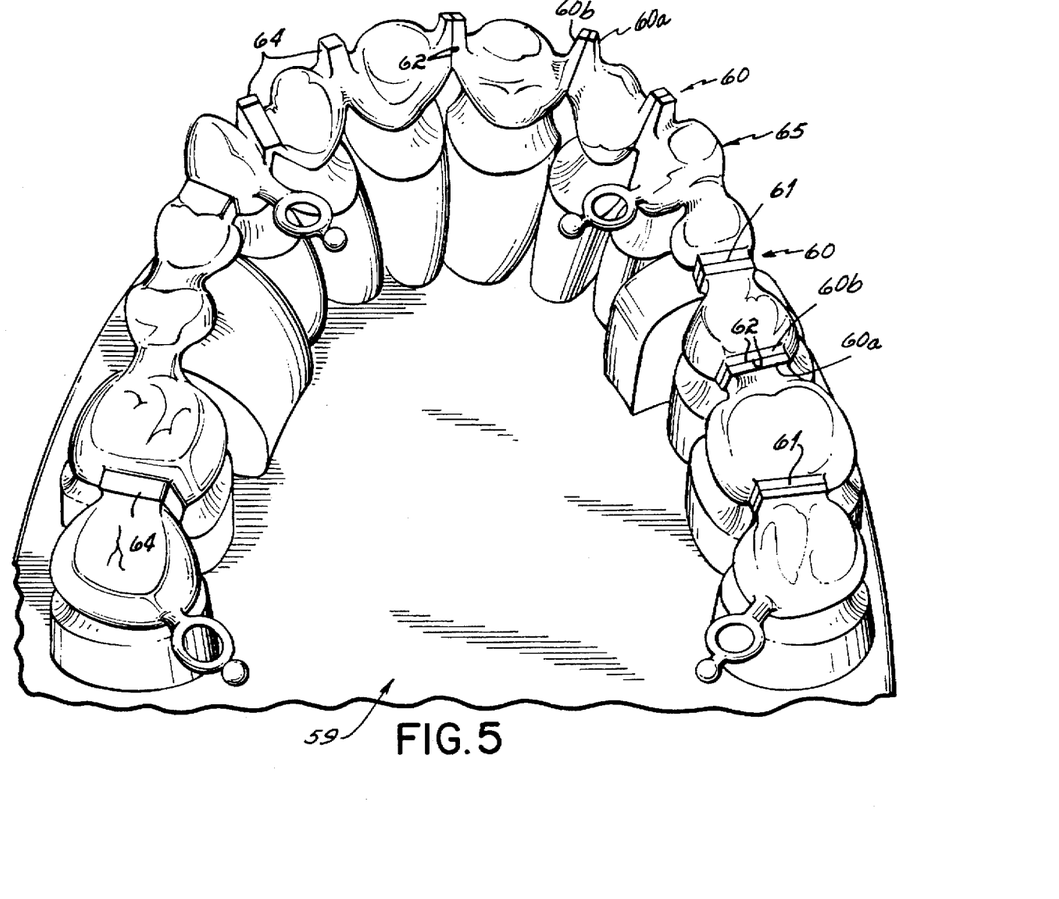
FIG. 5 is a perspective view of a working dental model of the metal framework of a dental restoration, with the cast sections thereof arranged in the configuration of the final restoration, showing the sections on the right separate and arranged for welding and the sections on the left welded.

After the sections 55a–55e and other sections are cut from the sprue portions 55f, they are fit on the corresponding abutment dies to demonstrate proper fit. All of the cast sections 55 are placed onto the working model 59, as illustrated in FIG. 5, with cast laser connector members 60a in contact with adjacent corresponding connector members 60b of a two member laser connector 60. All of the sections 55, when properly positioned on the model, will be in absolute contact at faces 62 between the members 60a,60b of laser connectors 60. In such positions, all sections 55 are ready for laser welding.

Laser welding is carried out with available laser welding equipment, such as the Excel LaserWelder™, which is a neodymium YAG 4 kW peak power pulsed laser of a type manufactured for dental applications by Excel Technology, Inc. of Hauppauge, N.Y., and distributed by American Recovery of Carle Place, N.Y.. The details of the laser and the manner of using it are known in the art, and are, for example, described in the Excel LaserWelder Dental Laboratory Technique Manual published by American Recovery, hereby expressly incorporated herein by reference. Such a laser, when aimed at edge of the junction 61 (FIG. 5) between fusible faces 62 of mating members 60a,60b of a cast connector 60, parallel to the faces 62, will melt the metal from the opposed faces surfaces and fuse, or more particularly, weld the metal faces together. The bond will penetrate to at least 1.5 mm along the face from one edge thereof, which is at least half way along the faces 62, but not entirely through to the other edge of the faces 62. When each of the connectors has been welded from one side, the entire framework can be removed as a unit from the model and inverted so the faces 62 can be welded from the other side, thereby accomplishing a weld of the entire 3 mm wide faces 62, forming solid, fused, one piece connectors 64, and a one-piece framework 65.

When the entire metal framework 65 has been laser welded and is in one piece, it is placed on the master model where it is ground to its final framework shape. Then it is veneered with ceramic porcelain or is otherwise subjected to selected finishing steps to form the completed restoration that is used to restore the patient's dentition.

From the above description of the preferred embodiments of the invention, it will be apparent to one skilled in the art that variations and modifications can be made without departing from the principles of the invention.

Accordingly, the following is claimed:

1. A method of forming a one piece dental restoration having a rigid structure of a prescribed configuration for connection to the dental anatomy of the patient on at least two points fixed relative thereto, the method comprising the steps of:

shaping a wax pattern of at least two wax components, each component including a wax retainer of a shape configured for rigid attachment to a respective one of the points, the pattern including a wax link formed of two wax elements, each element being fixed to one of the components and each having thereon an interface surface that lies in intimate contact with the interface surface of the other element when the components are arranged in the prescribed configuration;

by a lost wax investment casting process:
forming separate mold cavities from each of the wax components of the wax pattern, and
casting separate restoration sections, one in each of the cavities, each of the cast sections corresponding in shape to one of the components of the pattern and each having a fusible face thereon corresponding to the interface surface of the pattern component from which was formed the cavity in which the restoration section was cast;

arranging the restoration sections in the prescribed configuration with the fusible faces of adjacent sections in intimate mutual contact;

fusing the fusible faces of the restoration sections together to form a one-piece rigid structure of the prescribed configuration; and finishing the rigid structure to form the dental restoration.

2. The method of claim 1 wherein the casting step comprises the step of:

casting the separate restoration sections from metal.

3. The method of claim 1 wherein:

the casting step includes the step of casting the sections with the fusible face being a weldable face; and the fusing step includes the step of laser welding the weldable faces of adjacent sections together.

4. The method of claim 1 wherein:

the casting step includes the step of casting the sections of a material of which the fusible face is fusible with localized energy directed thereon; and the fusing step includes the step of directing localized energy onto a common place combining the fusible faces to fuse the faces together.

5. The method of claim 4 wherein:

the casting step includes the step of casting the sections of a weldable material; and the directing step includes the step of focusing a laser beam of the energy onto the fusible faces and laser welding the faces together therewith.

6. The method of claim 1 wherein the shaping step includes the steps of:

forming the wax pattern as an integral form that includes at least two wax retainers, each retainer configured for rigid attachment to the dental anatomy of the patient at a respective one of the points, the retainers being interconnected by an intermediate wax connector;

separating the pattern into the components by removing a transverse segment of fixed thickness from the connector to form a fixed thickness transverse slot through the connector, the slot being defined by confronting ends of the cut connector; and joining a wax filler blank, formed of two separable blades having the interface surfaces thereon in intimate contact with each other, having a thick body combined thickness approximately equal to the fixed thickness of the slot, to the pattern by inserting the blades of the wax filler blank into the slot between the confronting ends of the cut connector and by waxing each blade to a respective one of the confronting ends on each respective wax component, so that each of the blades forms one of the elements of the wax link, with the respective interface surfaces in intimate contact with each other.

7. The method of claim 6 wherein the separating step includes the step of cutting the slot of the fixed thickness through the intermediate wax connector.

8. The method of claim 1 wherein the restoration is a dental bridge including each cut two cut retainers each being configured to rigidly mount to a fixed abutment at a respective one of the points, the bridge having a bridging member including at least one pontic and at least two connectors fixed between one of the retainers and the at least one pontic, and wherein:

the shaping step includes the step of forming one of the two wax components to include one of the elements of the wax link, at least one wax pontic and one of the wax retainers and the other of the two components to include another one of the wax retainers and the other of the elements of the wax link.

9. The method of claim 1 further comprising the step of:
providing a preformed wax connector blank that includes a pair of confronting blades, each having one of the interface surfaces thereon and lying in intimate contact with the interface surface on the other, the blades being detachably joined together to form the blank;
the shaping step including the steps of interposing the blank between two components of the wax pattern and waxing to each component a respective one of the blades, so that each blade of the blank forms one of the elements of the wax link.

10. The method of claim 1 wherein the shaping step further includes the steps of:
forming the wax pattern as an integral form that includes the at least two wax retainers, each configured for rigid attachment of a cast section formed therefrom to the dental anatomy of the patient at a respective one of the points, the wax retainers being interconnected by an intermediate wax connector; and
separating the pattern into the components by removing a transverse segment of fixed thickness from the connector to form a fixed thickness transverse slot through the connector, the wax link having a thickness approximately equal to the fixed thickness of the slot and being positioned therein.

11. The method of claim 10 wherein the separating step includes the step of cutting the connector to form the fixed thickness slot.

12. The method of claim 10 wherein the link is approximately 3 mm in width.

13. The method of claim 1 wherein:
the casting step includes the step of casting the sections with the fusible face being a weldable face bounded by an edge; and
the fusing step includes the step of focusing, at the edge and parallel to the faces, a laser beam having an effective welding depth, and therewith laser welding the weldable faces of adjacent sections together across the faces to the effective welding depth; and
the shaping step includes the step of shaping the pattern such that the interface surfaces are each bounded by an edge corresponding to the edge of the weldable faces with every point on the entire area of each interface surface being within the effective depth of the nearest point on its edge.

14. The method of claim 13 wherein:
the shaping step includes the step of shaping the pattern such that no point on the edge of an interface surface is less than the effective depth of a point directly opposite on the edge thereof.

15. The method of claim 13 wherein:
the shaping step includes the step forming the interface surfaces to a rectangular shape having the shorter sides thereof equal in length to at least the effective depth and not more than twice the effective depth.

16. The method of claim 13 wherein:
the effective welding depth of the laser beam is 1.5 mm; and
the shaping step includes the step forming the interface surfaces to a rectangular shape having the shorter sides thereof equal in length to more than 1.5 mm and not more than 3 mm.

17. A dental restoration manufactured according to the method of claim 13.

18. A dental restoration manufactured according to the method of claim 1.

19. A dental restoration comprising:
at least two separate single castings each including at least one retainer;
at least two connector segments, each having a proximate end integral with a respective one of the segments and a remote end, the remote ends of the two connector segments being spaced apart relative to each other a fixed distance;
two blades, each having an inner confronting face parallel to and in intimate welded contact with the confronting face of the other, each blade having an outer surface generally parallel to its inner face, the blades being disposed between the spaced apart remote ends of the connector segments with the outer surface thereof being integral with the remote end of the respective connector segment, the blades having a collective thickness, measured perpendicular to the inner face and outer surfaces thereof, that is equal to the fixed distance between the remote ends of the connector segments; and
whereby each connector segment and the retainer and blade that are integral therewith form a respective one of the at least two single separate castings.

20. A wax pattern, for use in fabricating a dental restoration by a lost wax investing casting method, comprising:
at least two separate wax pattern components each including at least one wax retainer;
a wax link including two wax blades detachably connected together, each blade having an interface surface parallel to and in intimate contact with the interface surface of the other blade, each blade having a back surface generally parallel to its interface surface and waxed to a respective one of two of the at least two pattern components, with the link being disposed between the two pattern components.

21. A method of laser welding a one piece dental restoration comprising the steps of:
providing a preformed wax connector blank that includes a pair of confronting and detachably joined blades each having an interface surface thereon and lying in intimate contact with the interface surface on the other;
shaping a wax pattern of at least two detachably joined wax components having a wax link formed of the blank, with each of the blades of the blank being waxed into a respective one of the components;
separating the pattern into the two components by detaching the two blades of the blank;
separately casting restoration sections, one from each of the pattern components, with each of the cast sections having a weldable face thereon corresponding to the interface surface of the pattern component from which it was cast;
arranging the restoration sections with the weldable faces in intimate mutual contact; and
laser welding the faces together to form a one-piece rigid structure of a dental restoration.

22. The method of claim 21 wherein:
the casting step includes the step of casting the sections with the weldable faces being bounded by an edge; and
the laser welding step includes the step of focusing, at the edge and parallel to the faces, a laser beam having an effective welding depth, and therewith laser welding the weldable faces of the sections together across the faces to the effective welding depth; and
the shaping step includes the step of shaping the pattern such that the interface surfaces are each bounded by an edge corresponding to the edge of the weldable faces with every point on the entire area of each interface surface being within the effective depth of the nearest point on its edge.

23. The method of claim 22 wherein:

the shaping step includes the step of shaping the pattern such that no point on the edge of an interface surface is less than the effective depth of a point directly opposite on the edge thereof.

24. The method of claim 23 wherein:

the welding step includes the step of generating the laser beam with a neodymium YAG laser;

the effective welding depth of the laser beam is 1.5 mm; and the shaping step includes the step forming the interface surfaces having dimensions from 1.5 mm to 3 mm.

* * * * *